United States Patent [19]

Iacone

[11] Patent Number: 5,098,420
[45] Date of Patent: Mar. 24, 1992

[54] ONE-PIECE ILEOSTOMY OR COLOSTOMY BAG CONNECTOR

[76] Inventor: Daniel J. Iacone, Box 849, Berryville, Va. 22611

[21] Appl. No.: 611,014

[22] Filed: Nov. 9, 1990

Related U.S. Application Data

[63] Continuation-in-part of Ser. No. 119,712, Nov. 12, 1987.

[51] Int. Cl.⁵ ............................................... A61F 5/44
[52] U.S. Cl. ..................................................... 604/338
[58] Field of Search ............... 604/332, 337, 338, 339, 604/342, 345

[56] References Cited

U.S. PATENT DOCUMENTS

| 2,536,036 | 1/1951 | Cloninger | 604/332 |
| 2,584,540 | 2/1952 | Botvin et al. | 604/342 |
| 2,585,716 | 2/1952 | Zaetz | 604/342 |
| 2,655,153 | 10/1953 | Klotz . | |
| 2,692,597 | 10/1954 | Carstensen | 604/338 |
| 2,756,750 | 7/1956 | Pala . | |
| 2,818,069 | 12/1957 | Fenton | 604/338 |
| 3,283,757 | 11/1966 | Nelsen . | |
| 3,736,934 | 6/1973 | Hennessy | 604/342 |
| 3,856,011 | 12/1974 | Blanchard . | |
| 4,294,252 | 10/1981 | Einset . | |
| 4,319,571 | 3/1982 | Winchell . | |
| 4,460,363 | 7/1984 | Steer et al. | 604/342 |
| 4,592,750 | 6/1986 | Kay . | |
| 4,642,107 | 2/1987 | Arnone et al. . | |
| 4,648,875 | 3/1987 | Ferguson . | |
| 4,664,661 | 5/1987 | Ferguson . | |
| 4,723,952 | 2/1988 | Esposito . | |

FOREIGN PATENT DOCUMENTS

| 1105558 | 4/1961 | Fed. Rep. of Germany . | |
| 0345415 | 3/1960 | Switzerland | 604/332 |
| 2094154 | 9/1982 | United Kingdom | 604/345 |

Primary Examiner—Randall L. Green
Assistant Examiner—R. Clarke

[57] ABSTRACT

A one-piece bag connector for an ileostomy bag, colostomy bag or the like comprises an annular body portion, lip portion and a belt attachment. The body portion is adapted to surround a stoma of a user and the lip portion is connectable to a bag such that material may be discharged from the stoma to the bag without leakage. The body portion is made of resilient material and directly contacts the user thus avoiding the use of any gels or adhesive materials. The belt attachment connects a belt to the body portion such that a slight pressure is exerted against the user. This pressure plus the resilient nature of the body portion assures a proper seal between the user and the bag connector. Further, an easily attachable/detachable snap or screw connection is provided between the lip portion and the bag to assure a proper seal as well as convenience and ease in changing and/or removing the bag. The annular body portion, lip portion and belt attachment can be molded from plastic or the like to form the one-piece connector.

11 Claims, 5 Drawing Sheets

ONE-PIECE ILEOSTOMY OR COLOSTOMY BAG CONNECTOR

BACKGROUND OF THE INVENTION

This application is a Continuation-In-Part of application Ser. No. 07/119,712 filed Nov. 12, 1987.

FIELD OF THE INVENTION

The present invention relates to a one-piece connector for an ileostomy bag, a colostomy bag or the like. This one-piece connector includes an annular body portion, a lip portion and a belt attachment means.

DESCRIPTION OF THE BACKGROUND ART

In the treatment of human diseases and ailments, it is sometimes necessary to form an opening in the patient's anatomy and to maintain that opening for an indefinite period of time. For instance, diseases involving different parts of the gastro-intestinal and urinary tract can result in a patient being left with an abdominal stoma. The three most common types of abdominal stomas are the colostomy, the ileostomy and the ileal conduit. In the case of an ileostomy, ileal conduit and many colostomy operations, the patient is unable to control the passage of bodily waste material and must rely upon an appliance attached to the body to collect this material.

Various appliances have been proposed in the prior art. A majority of these appliances involve the use of gels or other adhesive materials which must be placed between the skin of the user and the bag connector. However, these gels are often messy to apply and are often inadequate to prevent leaks. For instance, if a user perspires, such as after exercise or on a hot day, these gels or adhesive materials are often ineffective in providing a leak-proof seal.

Further, many of the prior art arrangements are rather complicated to operate because they require a user to assemble various components. Thus, the user tends to avoid changing the ileostomy or colostomy bag and bacterial infections or other problems may arise. Further, as a complicated sealing arrangement is required, it is often difficult for the bag to be properly attached to the multi-piece connector and leaks may therefore arise.

Furthermore, such multi-piece complicated arrangements may be time consuming and may be difficult for certain users, such as elderly, handicapped or impaired persons or those with arthritis, to use. Over time, these multi-piece prior art constructions are subject to wear. Due to their multi-piece constructions, this wear can result in leaking of the prior art connectors. Furthermore, the manufacturing cost for these multi-piece prior art connectors tend to rise because of the need for manufacturing and packaging of several different components.

Accordingly, a need exists in the art for a simple and effective bag connector which is easy to operate, which avoids the use of gels and adhesive materials and which provides a reliable leak-proof seal.

SUMMARY OF THE INVENTION

Accordingly, it is the primary object of the present invention to Provide a one-piece bag connector which is simple to use and which provides an effective seal.

It is a further object of the present invention to provide an improved one-piece bag connector which can be placed adjacent a surgical opening to collect and hold any discharge from that opening.

It is yet another object of the present invention to provide a bag connector which is of one-piece construction, thereby avoiding the need for complicated assembly by the user and avoiding the possibility of losing any of the various parts making up the connector.

A further object of the present invention is to provide a one-piece connector which is sturdier and less prone to wear than multi-piece connectors.

It is another object of the present invention to provide a one-piece bag connector which does not require the use of gels or adhesive materials but which provides a leak-proof seal.

It is yet a further object of the present invention to provide a one-piece bag connector which may be worn by a user beneath his or her clothing and yet will be undetectable.

It is still another object of the present invention to provide a one-piece bag connector which permits its user to be active without the fear of developing a leak.

Yet another object of the present invention is to provide a one-piece bag connector which may be designed to fit a variety of sizes and shapes of people having different sized stomas, including infants and obese people.

It is still another object of the present invention to provide a one-piece connector which is easily used by arthritic, handicapped or impaired users.

Still another object of the present invention is to provide a one-piece bag connector which is inexpensive and simple to manufacture and which is easier to package than a connector having many components.

Another object of the present invention is to provide a one-piece connector which requires limited or no maintenance.

These and other objects of the present invention are fulfilled by providing a one-piece bag connector for connecting an ostomy bag about a stoma of a user. This one-piece connector includes an annular body portion with a lip portion located on the top side thereof. This annular body portion has a central opening which the lip portion encircles. The bottom side of the annular body portion may be placed directly against the user and this body portion has a sufficient thickness to allow movement of internal body portions adjacent the stoma during discharge of material from the stoma to the bag. The lip portion provides for a snap or screw attachment to a coupling member on the bag in order to form a leak-proof seal. The body portion has a rigid belt attachment to which a belt may be affixed. This belt provides slight pressure against the user such that the pressure along with the resiliency of the body portion will provide an effective, leak-proof seal between the body portion and the user. The annular body portion, lip portion and belt attachment means are all a rigid, one-piece construction forming the connector.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE PREFERRED EMBODIMENT

Figure 1:
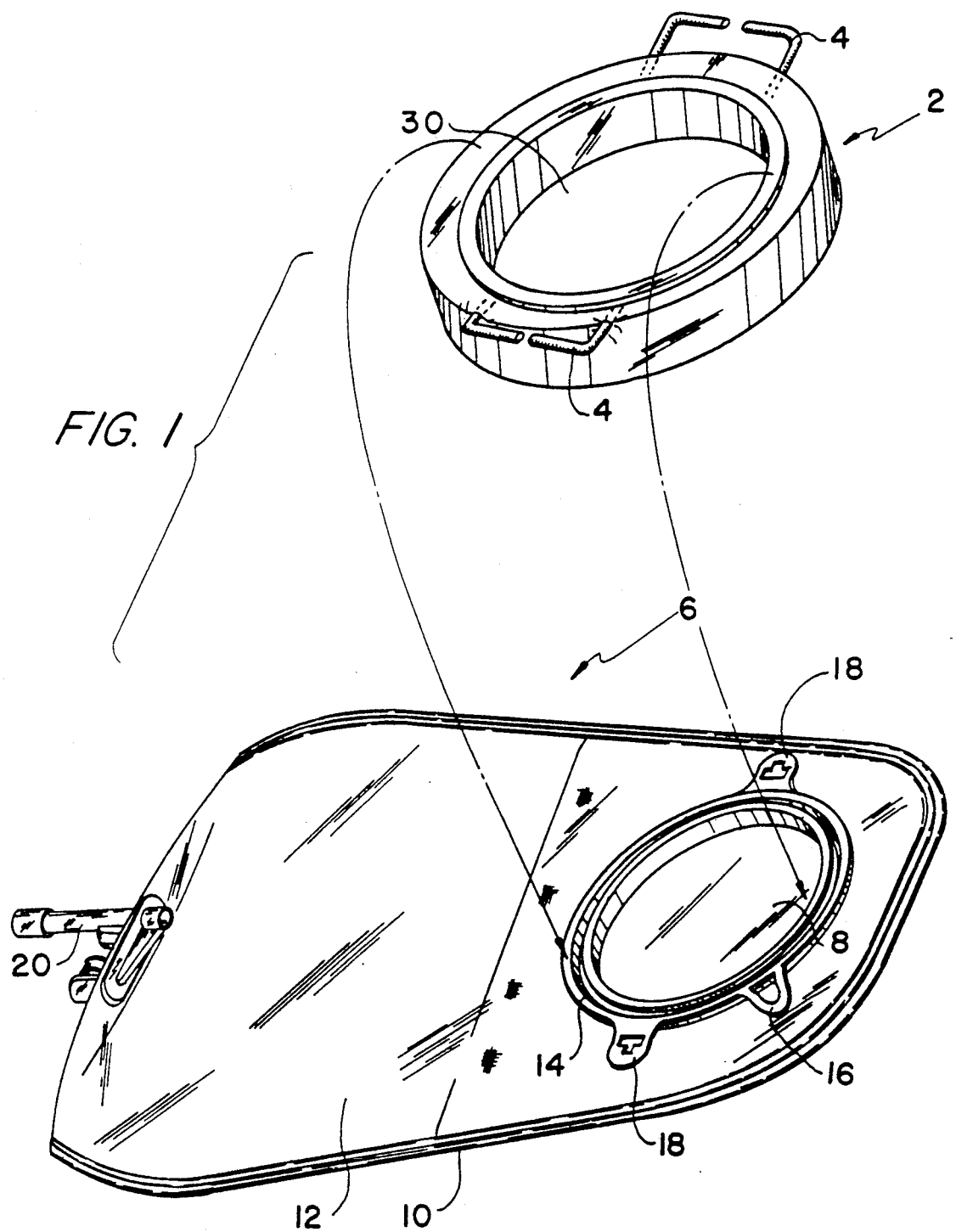
FIG. 1 is a perspective view of the one-piece bag connector of the present invention and of the bag prior to attachment to the connector.

Referring in detail to the drawings and with particular reference to FIG. 1, an annular one-piece bag connector 2 is shown. This connector has a generally rigid belt attachment means 4 located on opposite sides thereof. A central opening 30 is provided in this one-piece connector 2. The ostomy bag 6 is also shown in FIG. 1. This ostomy bag may be an ileostomy bag, a colostomy bag or the like. While this bag will be referred to hereinafter as an ileostomy bag, it should be understood that any suitable collecting apparatus for receiving bodily discharge from a stoma may be used.

The ileostomy bag 6 has a bag aperture 8. The bag consists of a front bag wall 10 and a rear bag wall 12. Rear bag wall 12 has an aperture 8 for passage of bodily wastes from the stoma. This aperture 8 is surrounded by a coupling member 14. This coupling member 14 may be permanently affixed to the bag wall 12 by heat sealing. Channel shaped coupling member 14 includes a pull tab 16 and pull tab ears 18 as shown in FIG. 1, but it should be understood that this tab 16 and ears 18 can be omitted. The tab and tab ears may be used to aid attachment and removal of the bag 6 to the bag connector 2. Ileostomy bag 6 is shown as having a bottom drain valve opening 20. This bag may be of a disposable type, or it may be a reusable type bag.

Figure 2:
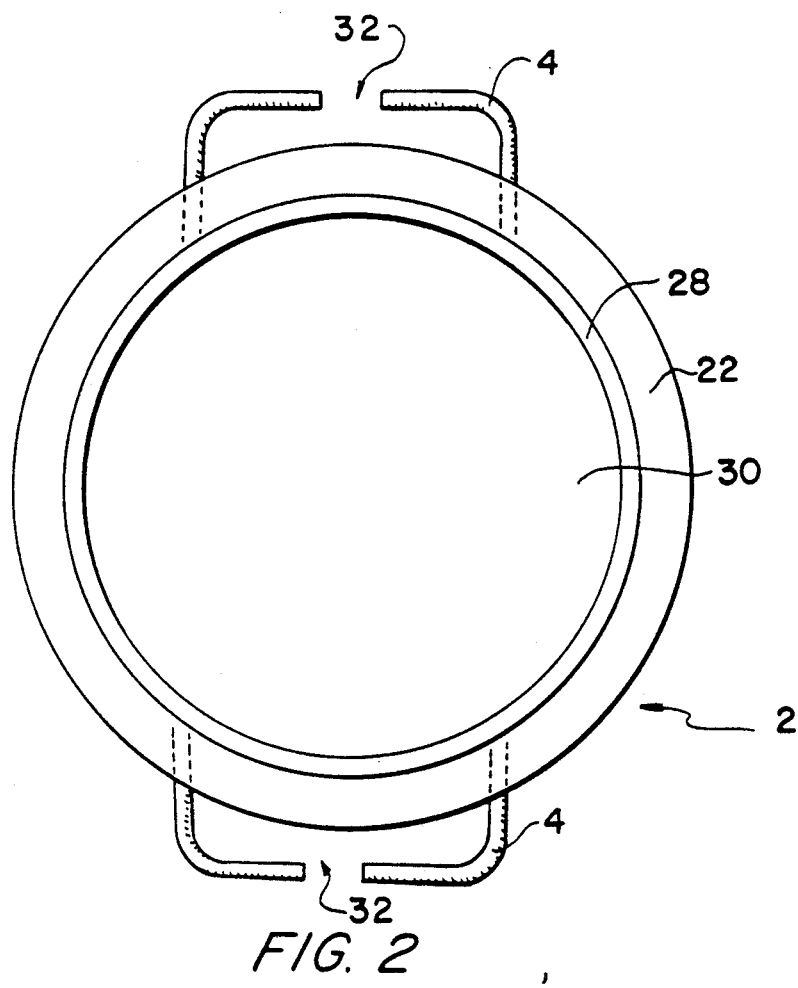
FIG. 2 is a plan view of the one-piece bag connector shown in FIG. 1.
Figure 3:
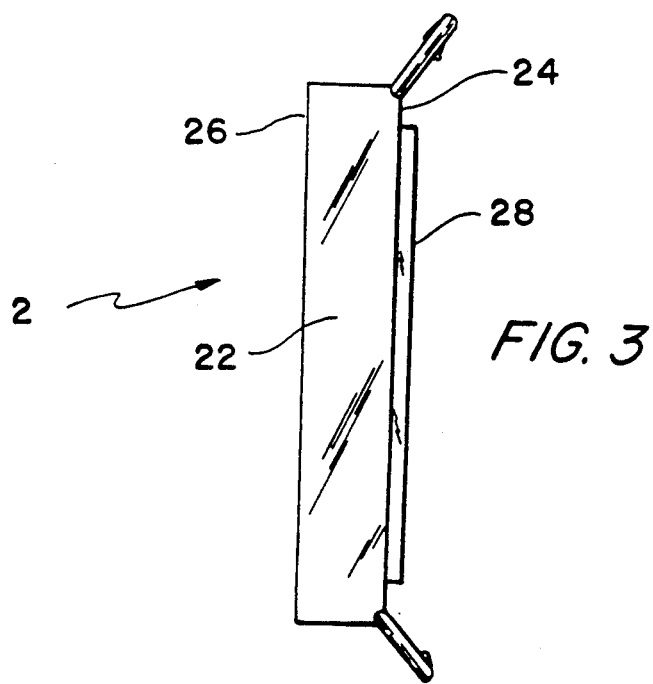
FIG. 3 is a side view of the one-piece bag connector of the present invention.

As seen in FIGS. 2 and 3, the bag connector 2 has an annular body portion 22 having a top side 24 and a bottom side 26. This bottom side 26 is designed to directly contact the skin of the user. Annular body portion 22 may be fabricated from a resilient material. This material may include a pharmaceutically acceptable substance such as a silicone material or the like. As the body portion 22 directly contacts the user on its bottom side 26, the resilient composition of the body portion aids in forming a leak-proof seal between the user and the bag connector.

Annular body portion 22 also has a raised lip portion 28. The annular body portion 22 and raised lip portion 28 can be fabricated by molding or the like. These portions 22 and 28 are of a one-piece construction. Thus, assembly of these portions by a user is unnecessary. Also, a relatively rigid, non-flexible connector is thereby formed.

This raised lip portion 28 is designed for attachment to the coupling member 14 of the ileostomy bag 6. This raised lip portion 28 has a generally smooth outer side and top which enables the coupling member 14 to snap onto lip portion 28. A leak-proof seal between the body portion 22 and the bag 6 is therefore formed. Such a seal prevents escape of discharged wastes from the bag 6. This connection arrangement is easy to effectuate and may be quickly carried out by a user. This connection arrangement merely requires that the bag connector be snapped onto the lip 28. Such an arrangement does not require great dexterity by the user but will provide for an effective seal. This feature is especially useful for arthritic, handicapped or impaired users.

The annular body portion 22 also has a belt attachment means 4 connected thereto. While a metallic belt attachment means 4 embedded in the resilient material of body portion 22 is used, this belt attachment means 4 can be molded from the same material as body portion 22 and lip portion 28 as will be discussed below. The belt attachment means 4, the annular body portion 22 and the raised lip portion 28 all form a unitary one-piece structure. Thus, this arrangement is inexpensive to manufacture and does not require complicated assembly or disassembly by a user and loss of small disassembled parts of the device is avoided because the connector is a one-piece construction. Such an arrangement also avoids formation of gaps between abutting elements and thus ensures a leak-proof arrangement. Also, this one-piece design avoids wear of the connector over time such that the sealing integrity can be maintained. Further, precise manufacturing accuracy is not required in forming the bag connector and assembly during manufacture is simple.

Figure 4:
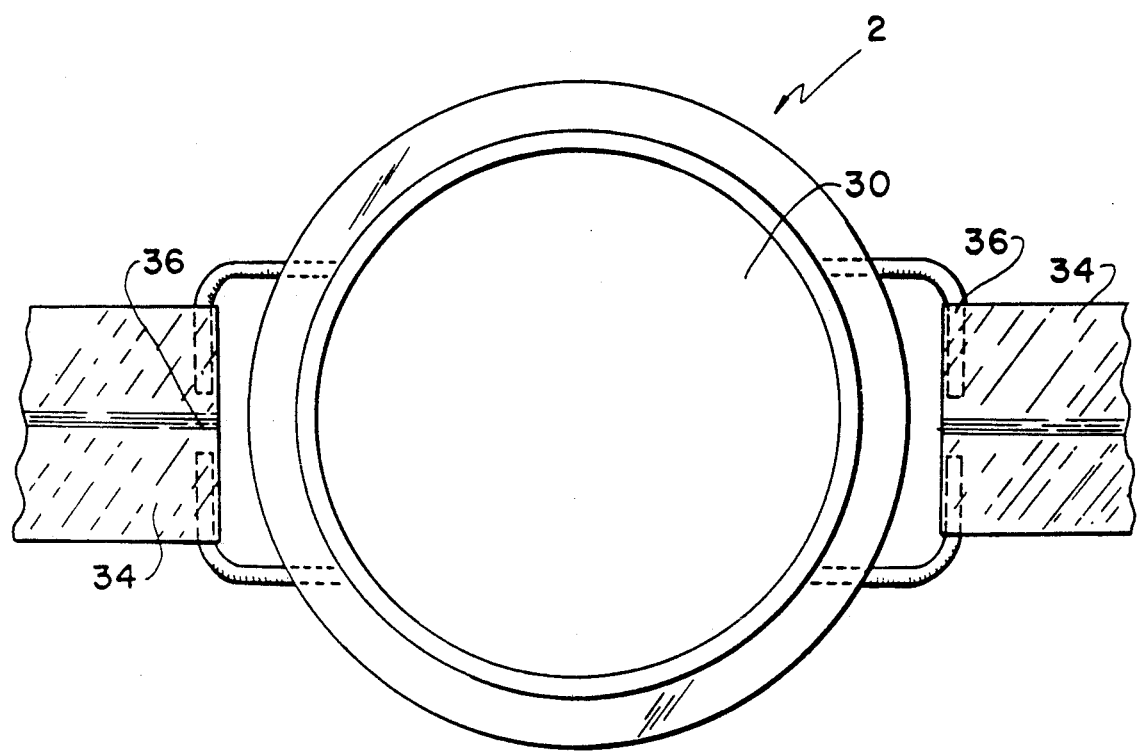
FIG. 4 is a plan view of the one-piece bag connector of the present invention with a first belt attachment arrangement.
Figure 5:
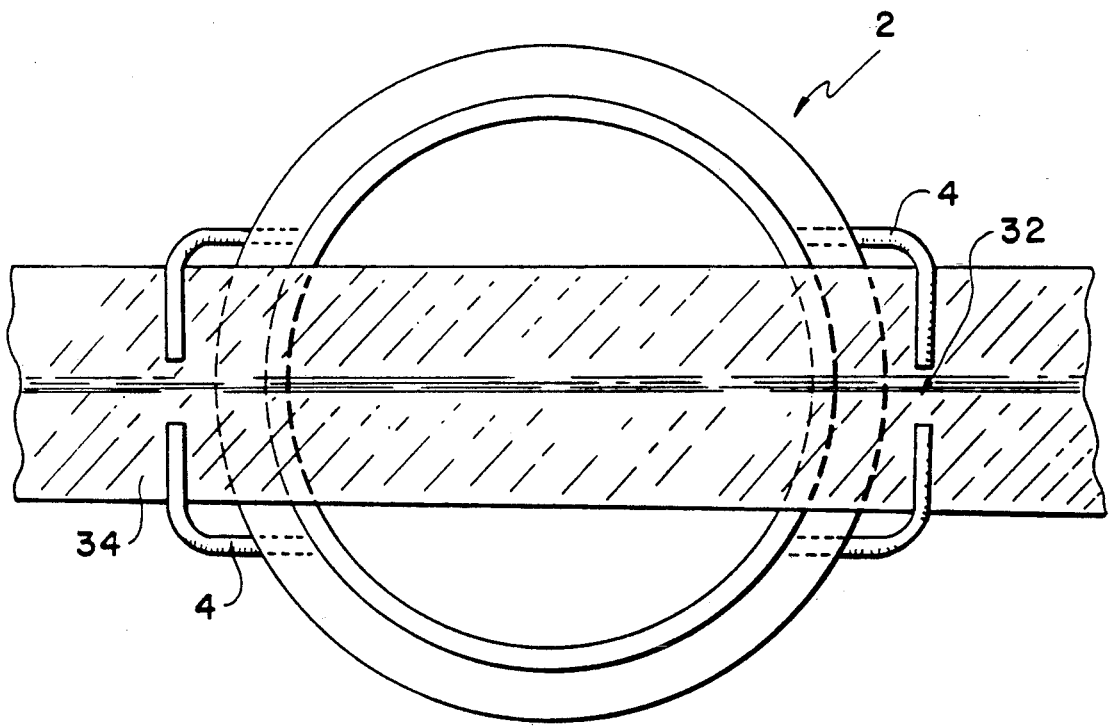
FIG. 5 is a plan view of the one-piece bag connector of the present invention with a second arrangement for the belt connection.

As seen in FIGS. 4 and 5, various arrangements for attaching a belt 34 to the bag connector 2 are shown. In particular, in FIG. 4, the belt 34 has two belt end portions 36. These end portions may be sewn or otherwise attached so as to form loops at the ends thereof. The belt attachment means 4 is provided with two hooks on each side of the annular body portion 22. These hooks have a belt attachment opening 32 therebetween as seen in FIG. 2. As can be seen in FIG. 4, the looped portion of each belt end 36 may be slipped into the hooks of the belt attachment means 4. This arrangement provides for unobstructed access to the body portion opening 30.

As seen in FIG. 5, an alternative arrangement involves weaving the belt 34 through the belt attachment means 4. In operation, the belt will rest over the annular body portion 22 as well as the bag 6 attached to the lip portion 28. In order for the belt 34 overlying body portion opening 30 to be in a position avoiding interference with discharge from the stoma, the thickness of the body portion 22 can be increased during manufacture of the connector 2 such that the distance from the belt 34 to the stoma is increased. Also, the width of the belt can be decreased in the area of central opening 30 to reduce the possibility that this belt may interfere with waste discharge.

In either of the arrangements shown in FIG. 4 or FIG. 5, the belt will connect to the one-piece bag connector 2 and will extend around the body of the user. A suitable clasp means (not shown) may be provided for enabling the user to fasten and unfasten the belt. In both of the arrangements shown in FIGS. 4 and 5, the belt will firmly hold the bag connector against the body of the user. This will cause a slight pressure to be exerted toward the user. This pressure along with the resilient material forming the annular body portion 22 will form a leak-proof seal between the body portion 22 and the user. This seal thus avoids the use of gels or other adhesives for causing the bag connector to adhere to the user.

The arrangement of the present invention avoids the problems encountered when using gels or adhesives as leaks developing when the user is active and perspires. Greater freedom of movement may be obtained by a user of the instant device. The user will be able to participate in athletic events and do common, everyday activities which are often difficult for ileostomy bag wearers. For instance, the user of this device may easily climb a ladder, get into and out of a truck or other vehicle, or dance with a partner. All of these activities were often perilous for a user of a conventional bag connection arrangement as leaks would often occur. Such leaks may stain the clothes of the user, inhibit the user from participating in certain activities or at the very least embarrass the user. The present invention thus alleviates such problems and enables the user to fully participate in many activities which heretofore could not be done.

The one-piece bag connector of the present invention also provides for easy changing of bag 6 by a user. As this bag just snaps onto and off of the raised lip portion 28, a user may easily replace the bag in a few seconds without the need for undressing to any substantial degree. Further, the arrangement of the instant invention is compact such that it is undetectable beneath the clothes of a user. However, the annular body portion 22 of the instant invention is sufficiently thick to permit any internal body portions adjacent the stoma to freely move during discharge of waste. Such movement is a natural occurrence during discharge and is hindered by conventional connectors which are too flat. Accordingly, the annular body portion 22 of the instant invention may be approximately ¾ of an inch thick. However, it is contemplated that any thickness suitable for a particular person may be used. For instance, an infant may use a bag connector which is sized to the infant's needs. Likewise, an obese person may have a larger sized bag connector is necessary.

While the belt attachment means 4 of the instant invention is shown as having a belt attachment opening 32, each belt attachment may be a single element without such an opening. The belt 34 may also be permanently affixed to the belt attachment means or may have suitable conventional connectors to permit fastening and unfastening of the belt from the belt connector arrangement of FIG. 4. Likewise, the arrangement shown in FIG. 5 may omit the belt attachment opening 32 such that the belt 34 will merely be woven under each belt attachment means 4 but over the bag 6 and annular body portion 22.

Figure 6:
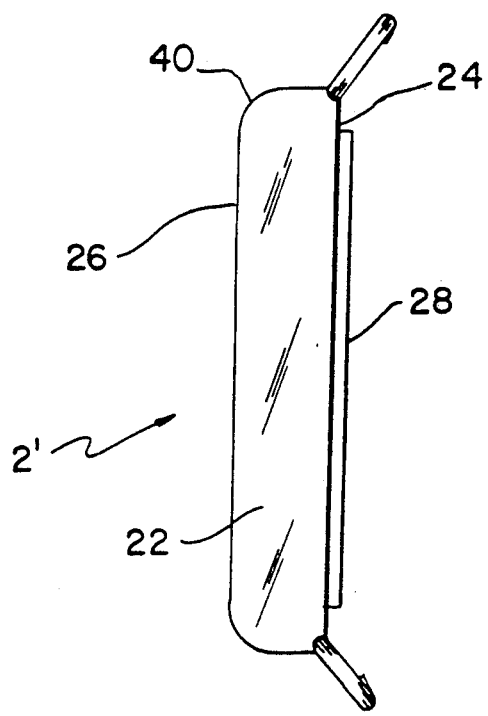
FIG. 6 is a side view of a modified form of the one-piece bag connector of the present invention.
Figure 7:
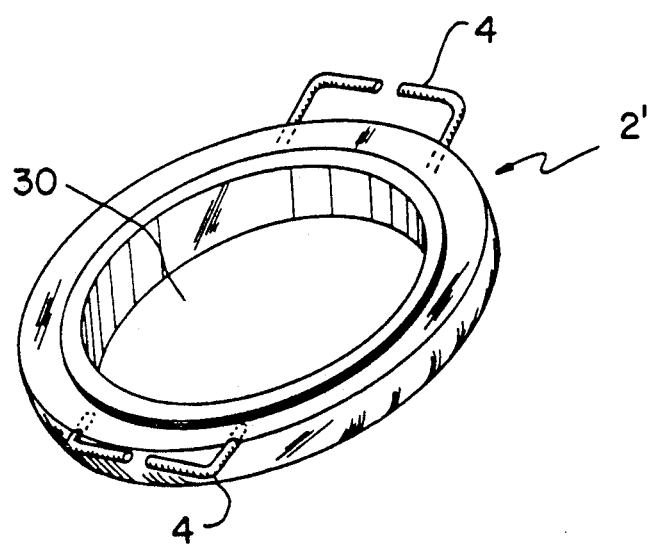
FIG. 7 is a perspective view of the one-piece bag connector as shown in FIG. 6.

As seen in FIGS. 6 and 7, a modified form of the one-piece connector is shown. This modified one-piece connector is labeled as 2' and differs from the above-discussed connector in that the bottom side 26 is beveled about its outer periphery 40. This beveled edge avoids irritation of the user by providing a more comfortable fit for the connector. This modified one-piece connector 2' is nonetheless as effective as the connector 2 and has all the same benefits.

Figure 8:
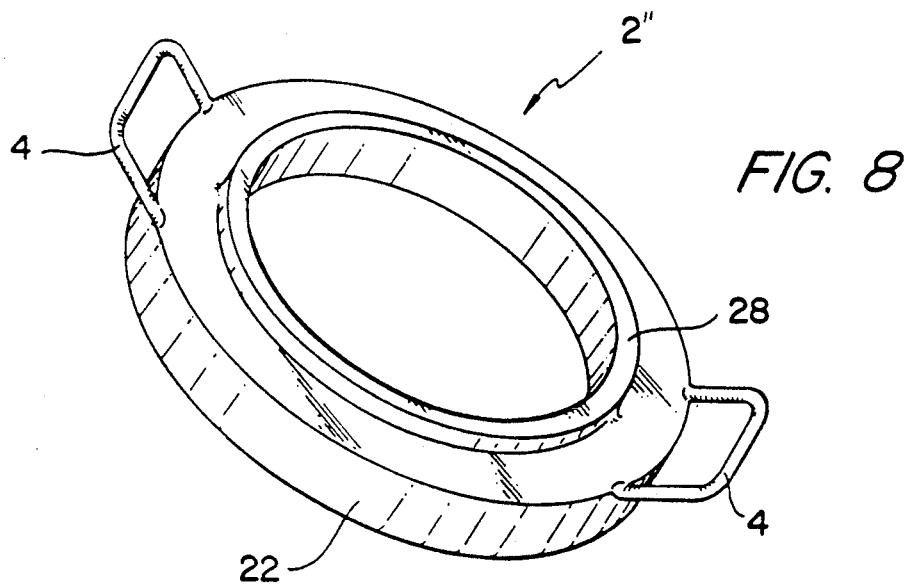
FIG. 8 is a perspective view of a second embodiment of the one-piece bag connector of the present invention.
Figure 9:
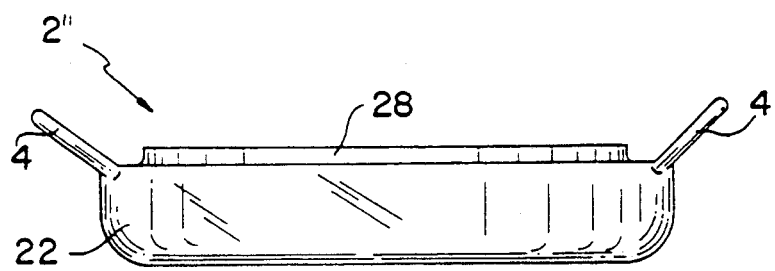
FIG. 9 is a side view of the one-piece bag connector shown in FIG. 8.

As further seen in FIGS. 8 and 9, a second embodiment of the one-piece connector is shown. This second embodiment one-piece connector is labeled as 2" in these FIGS. 8 and 9. This one-piece connector 2" differs from the above-discussed connectors in that the annular body portion 22, raised lip portion 28 and belt attachment means 4 are all made from the same material. In fact, this one-piece connector 2" can be molded from a silicone material, plastic or the like. Manufacture of this one-piece connector 2" is therefore simplified. Specifically, this connector 2" can be molded without the need for additional assembly steps. Therefore, manufacturing costs can be kept low. Also, because this connector 2" (like the previously discussed connectors) is of a one-piece construction, then this connector 2" is sturdier and less prone to wear over time than multi-piece connectors known in the prior art. For example, multi-piece connectors are known using riveted connections but these connections can wear over time, unlike that of the instant connector.

The second embodiment of the one-piece connector 2" shown in FIGS. 8 and 9 does not have an opening provided in the belt attachment means 4. This aids molding manufacturing of this connector 2". However, if so desired, an opening can be provided in the belt attachment means 4 like the previously discussed opening 32. Also, the bottom side of this connector is beveled like the embodiment shown in FIGS. 6 or 7. However, it should be understood that a bottom side like that used in the connector 2 shown in FIG. 1 can also be employed.

Figure 10:
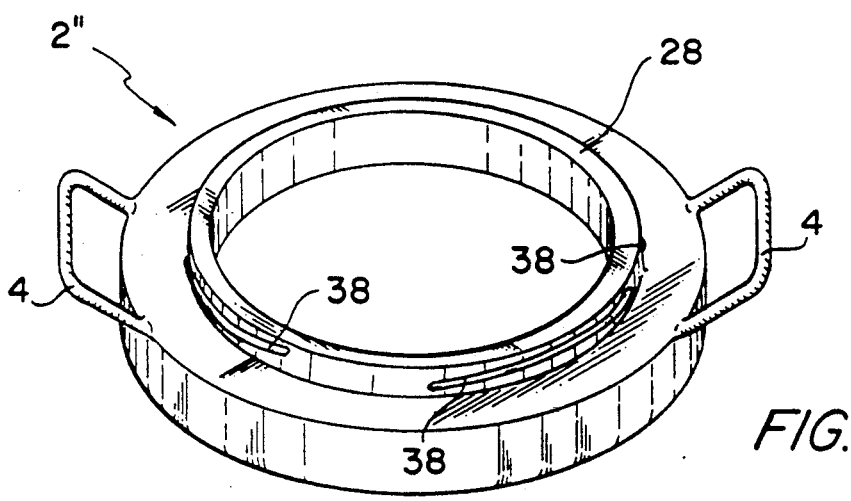
FIG. 10 is a perspective view of a modified form of the second embodiment of the one-piece bag connector of the present invention.

FIG. 10 shows a modified form of the second embodiment of the one-piece connector 2". This modification has a screw connection for the raised lip portion 28. Rather than snapping a bag 6 onto this connection, the coupling member 14 of the bag can be provided with a mating screw portion. In this manner, the bag 6 and one-piece connector 2" can be screwed together. FIG. 9 indicates a sequence of four screw threads 38 (only one complete thread and two partial threads being shown) provided on the raised lip portion 28. It should be understood, however, that only a partial screw thread, a single encircling screw thread or a screw thread encircling the raised lip portion 28 many times can be used. In other words, rather than simply attaching the bag 6 by screwing the bag 90° onto the connector 2", any other suitable number of turns of partial turns can be used for connecting the bag 6 to connector 2". Also, FIG. 10 indicates the four screw threads being in non-overlapping relation. However, these four threads (or any other combination of threads) could overlap such that an upper terminating end of one thread would be positioned vertically above another thread.

While the previously discussed one-piece connectors 2 and 2' have been shown with a raised lip portion 28 to which the bag is snapped, any of these other connectors can also be used with a raised lip portion having a screw thread. Provision of the screw thread 38 on the raised lip portion 28 has the same advantages of the snap-on arrangement previously discussed. A leak-proof seal is provided between the one-piece connector 2" and the bag 6. Escape of discharge waste from the bag 6 is prevented and quick connecting and disconnecting can be carried out with this one-piece connector 2" shown in FIG. 10. Again, great dexterity is not need by the user and even those users with arthritis or those users who are handicapped or are otherwise impaired can also easily use this connector 2" as seen in FIG. 10.

The bag connector of the present invention provides a satisfactory means for assuring collection of waste from a stoma of a user. This device increases the confidence of a user since leakage is prevented. Further, ease of use of this device is provided. Thus, elderly person or persons suffering from arthritis will find that the bag connector of the invention is easy and convenient to use.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A one-piece bag connector for connecting an ostomy bag about a stoma of a user, the bag having a coupling member surrounding an opening therein, said bag connector comprising:

an annular body portion having a top and bottom side, said bottom side being adapted to directly contact the user, said body portion having a central aperture which surrounds said stoma and permits unobstructed discharge of bodily wastes from said stoma, said body portion being formed from a resilient material;

a lip portion encircling said body portion aperture, said lip portion being located on the top side of said body portion and being detachably connectable with said coupling member of said bag such that said bag may be affixed directly to said body portion and such that discharge from the stoma to the bag is permitted; and belt attachment means for attaching a belt to said body portion, said belt attachment means being a rigid, one-piece construction with said body portion and said lip portion whereby assembly by the user is avoided, said belt attachment means having at least two hooks located on opposite sides of the body portion and extending above the top side of said body portion, the belt having two ends each having loop portions, each of said loop portions being attached to one of said hooks in order to attach said belt to said belt attachment means;

said lip portion, said belt attachment means and said body portion together forming a single unitary, one-piece structure, said belt attachment means permitting said belt to hold said body portion about said stoma such that a slight pressure is exerted against the user, said pressure and said resilient material forming said body portion permitting a substantially leak-proof seal to be formed between the user and said body portion, said lip portion and said coupling member of said bag further forming a leak-proof seal between said body portion and said bag;

wherein said one-piece connector is used with one of an ileostomy bag and a colostomy bag, the lip portion of the one-piece connector generally having a smooth outer side such that the one of the ileostomy bag and the colostomy bag can snap onto the lip portion to be sealed thereof, thereby forming the only connection between the bag connector and the bag.

2. The one-piece bag connector of claim 1, wherein said one-piece resilient material comprises a silicone material.

3. The one-piece bag connector of claim 1, wherein an outer periphery of said bottom side of said annular body is beveled.

4. The one-piece bag connector of claim 1, wherein the annular body portion, the lip portion and the belt attachment means are all the same material, the annular body portion, the lip portion and the belt attachment means being molded to form the one-piece connector which is of a single, unitary, one-piece construction.

5. The one-piece bag connector of claim 4, wherein the material of the bag connector is one of silicone and plastic.

6. The one-piece bag connector of claim 5, wherein the lip portion of the one-piece connector is provided with four threads.

7. A one-piece bag connector for connecting an ostomy bag about a stoma of a user, the bag having a coupling member surrounding an opening therein, said bag connector comprising:

an annular body portion having a top and bottom side, said bottom side being adapted to directly contact the user, said body portion having a central aperture which surrounds said stoma and permits unobstructed discharge of bodily wastes from said stoma, said body portion being formed from a resilient material;

a lip portion encircling said body portion aperture, said lip portion being located on the top side of said body portion and being detachably connectable with said coupling member of said bag such that said bag may be affixed directly to said body portion and such that discharge from the stoma to the bag is permitted; and belt attachments means for attaching a belt to said body portion, said belt attachment means being a rigid, one-piece construction with said body portion and said lip portion whereby assembly by the user is avoided, said belt attachment means having at least two hooks located on opposite sides of the body portion and extending above the top side of said body portion, the belt having two ends each having loop portions, each of said loop portions being attached to one of said hooks in order to attach said belt to said belt attachment means;

said lip portion, said belt attachment means and said body portion together forming a single unitary, one-piece structure, said belt attachments means permitting said belt to hold said body portion about said stoma such that a slight pressure is exerted against the user, said pressure and said resilient material forming said body portion permitting a substantially leak-proof seal to be formed between the user and said body portion, said lip portion and said coupling member of said bag further forming a leak-proof seal between said body portion and said bag;

said one-piece connector is used with one of an ileostomy bag and a colostomy bag, the bag having a coupling member with at least one thread thereon, the lip portion of the one-piece connector further comprising at least one thread along an outer side thereof, said at least one thread on the coupling member being in mating, sealing engagement with the at least one thread on the lip portion thereby forming the only connection between the one-piece connector and the bag when the coupling member is screwed onto the lip portion to mount the bag on the one-piece connector.

8. The one-piece bag connector of claim 7, wherein said one-piece resilient material comprises a silicone material.

9. The one-piece bag connector of claim 7, wherein said outer periphery of said bottom side of said annular body is beveled.

10. The one-piece bag connector of claim 7, wherein said annular body portion, the lip portion and the belt attachment means are all the same material, the annular body portion, the lip portion and the belt attachment means being molded to form the one-piece connector which is of a single, unitary, one-piece construction.

11. The one-piece bag connector of claim 7, wherein the material of the bag connector is one of silicone plastic.

* * * * *